United States Patent [19]

Vallelunga et al.

[11] Patent Number: 5,352,203

[45] Date of Patent: Oct. 4, 1994

[54] ASPIRATING NON-REUSEABLE SYRINGE

[76] Inventors: Anthony J. Vallelunga, 209 Schoolhouse Rd., Albany, N.Y. 12203-5956; Paul V. Cacciotti; Vincent E. Cacciotti, both of 9 Morgan Way, Latham, N.Y. 12110

[21] Appl. No.: 220,867

[22] Filed: Mar. 31, 1994

[51] Int. Cl.⁵ .................................................. A61M 5/00
[52] U.S. Cl. ............................. 604/110; 604/218; 604/228
[58] Field of Search ............ 604/110, 187, 218, 220, 604/228

[56] References Cited

U.S. PATENT DOCUMENTS

| | | | |
|---|---|---|---|
| 2,752,920 | 7/1956 | Kurkjian | 128/261 |
| 4,391,272 | 7/1983 | Staempfli | 604/110 |
| 4,758,232 | 7/1988 | Chak | 604/220 |
| 4,775,363 | 10/1988 | Sandsdalen | 604/110 |
| 4,775,364 | 10/1988 | Alles | 604/110 |
| 4,820,272 | 4/1989 | Palmer | 604/110 |
| 4,840,616 | 6/1989 | Banks | 604/110 |
| 4,863,427 | 9/1989 | Cocchi | 604/110 |
| 4,874,372 | 10/1989 | McArthur et al. | 604/110 |
| 4,878,899 | 11/1989 | Plouff | 604/110 |
| 4,883,466 | 11/1989 | Glazier | 604/110 |
| 4,915,692 | 4/1990 | Verlier | 604/110 |
| 4,932,941 | 6/1990 | Min et al. | 604/110 |
| 4,935,016 | 6/1990 | Deleo | 604/198 |
| 4,950,240 | 8/1990 | Greenwood et al. | 604/110 |
| 4,950,243 | 8/1990 | Estruch | 604/110 |
| 4,961,728 | 10/1990 | Kosinski | 604/110 |
| 4,973,308 | 11/1990 | Borras et al. | 604/110 |
| 4,973,309 | 11/1990 | Sultan | 604/110 |
| 4,978,339 | 12/1990 | Labouze et al. | 604/110 |
| 4,994,044 | 2/1991 | LoDuca | 604/192 |
| 5,000,735 | 3/1991 | Whelan | 604/110 |
| 5,019,045 | 5/1991 | Lee | 604/110 |
| 5,037,393 | 8/1991 | Ellgass | 604/110 |
| 5,059,179 | 10/1991 | Quatrochi et al. | 604/110 |
| 5,078,686 | 1/1992 | Bates | 604/110 |
| 5,084,017 | 1/1992 | Maffetone | 604/110 |
| 5,085,638 | 2/1992 | Farbstein et al. | 604/110 |
| 5,085,640 | 2/1992 | Gibbs | 604/110 |
| 5,088,987 | 2/1992 | Noonan, Jr. | 604/195 |
| 5,090,961 | 2/1992 | Maruzik et al. | 604/110 |
| 5,090,962 | 2/1992 | Landry, Jr. et al. | 604/110 |
| 5,114,405 | 5/1992 | Winter | 604/110 |
| 5,127,906 | 7/1992 | Landry, Jr. et al. | 604/110 |
| 5,135,495 | 8/1992 | Arcusin | 604/110 |
| 5,215,524 | 6/1993 | Vallelunga et al. | 604/110 |

FOREIGN PATENT DOCUMENTS

| | | |
|---|---|---|
| 0112893 | 1/1969 | Denmark . |
| 0325886 | 8/1989 | European Pat. Off. . |
| 1228933 | 9/1960 | France . |
| 2621824-A | 4/1989 | France . |
| 2646087 | 10/1990 | France . |
| 2653340 | 4/1991 | France . |
| WO89/12476 | 12/1989 | PCT Int'l Appl. . |
| WO90/07949 | 7/1990 | PCT Int'l Appl. . |

*Primary Examiner*—John D. Yasko
*Attorney, Agent, or Firm*—Heslin & Rothenberg

[57] ABSTRACT

An aspirating non-reuseable syringe is provided which includes a plunger. The main components of the plunger include a piston and a cylindrical plunger stem. The piston is removably connected to the cylindrical plunger stem by first, second, and third connecting members. The connecting members utilize a nipple mating with one aperture and sliding within another aperture to effect aspiration as well as disconnection of the piston from the plunger stem after a single use of the syringe.

5 Claims, 3 Drawing Sheets

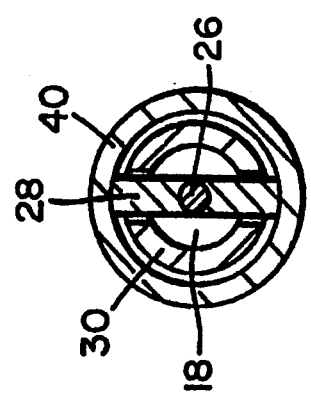
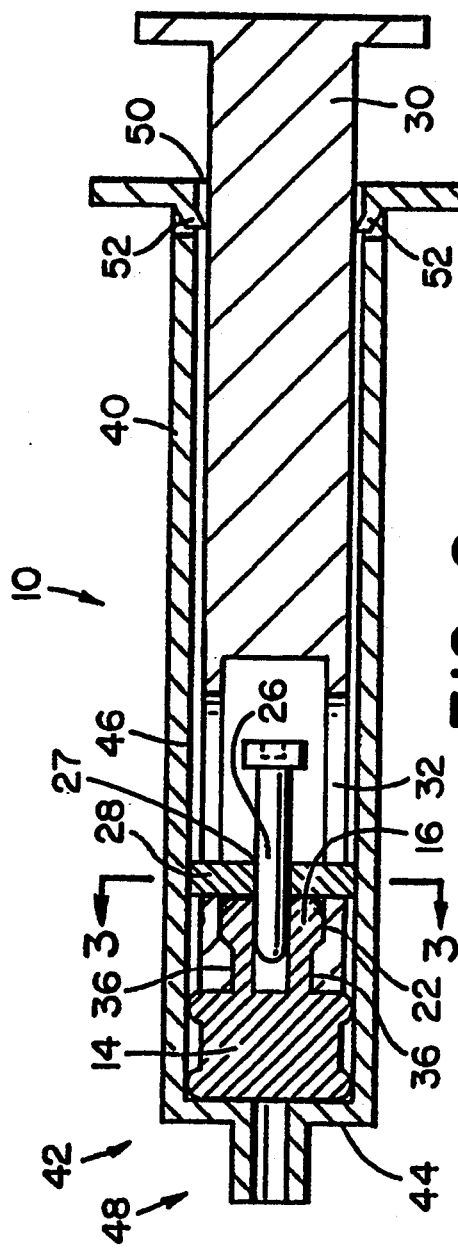
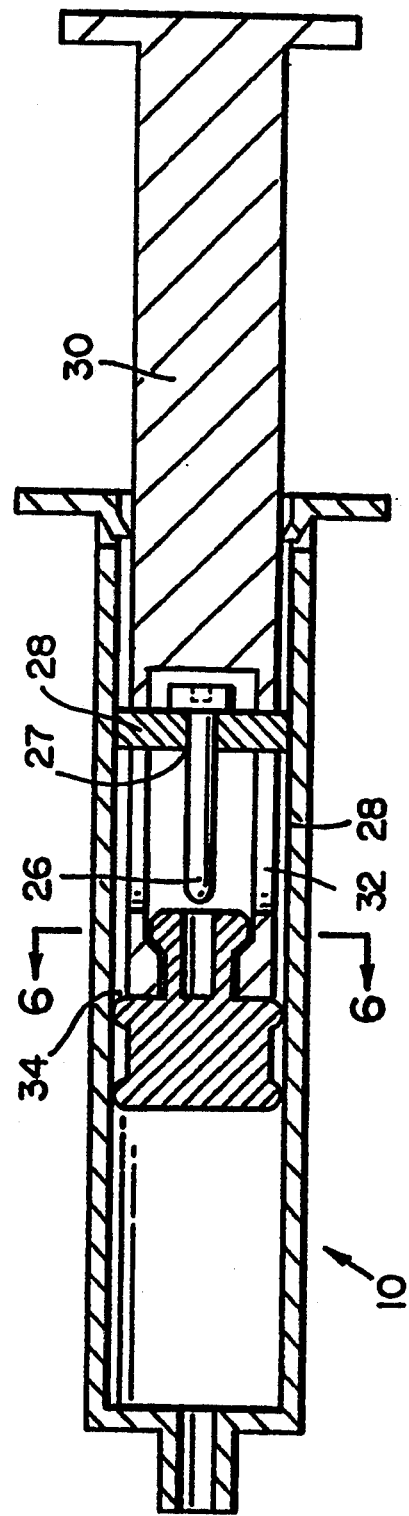

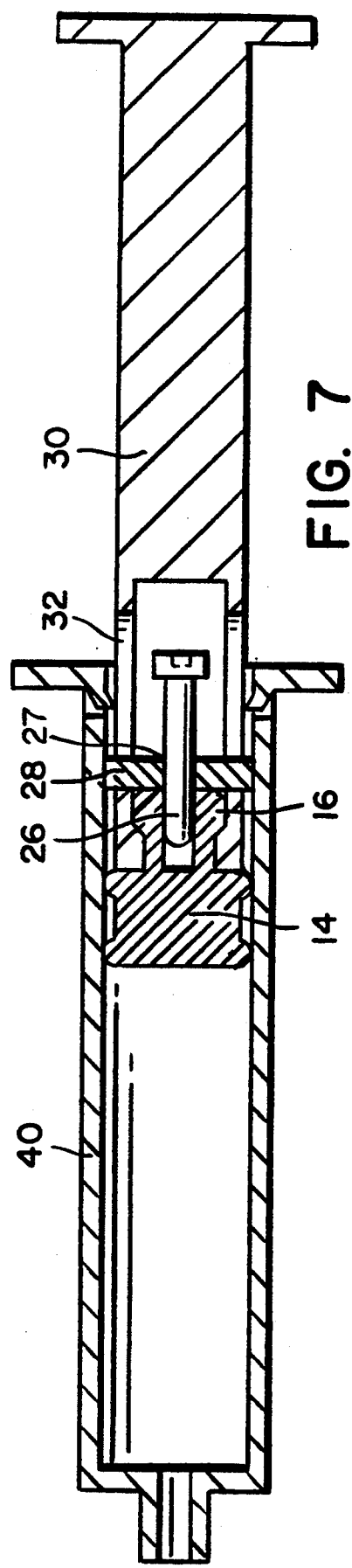
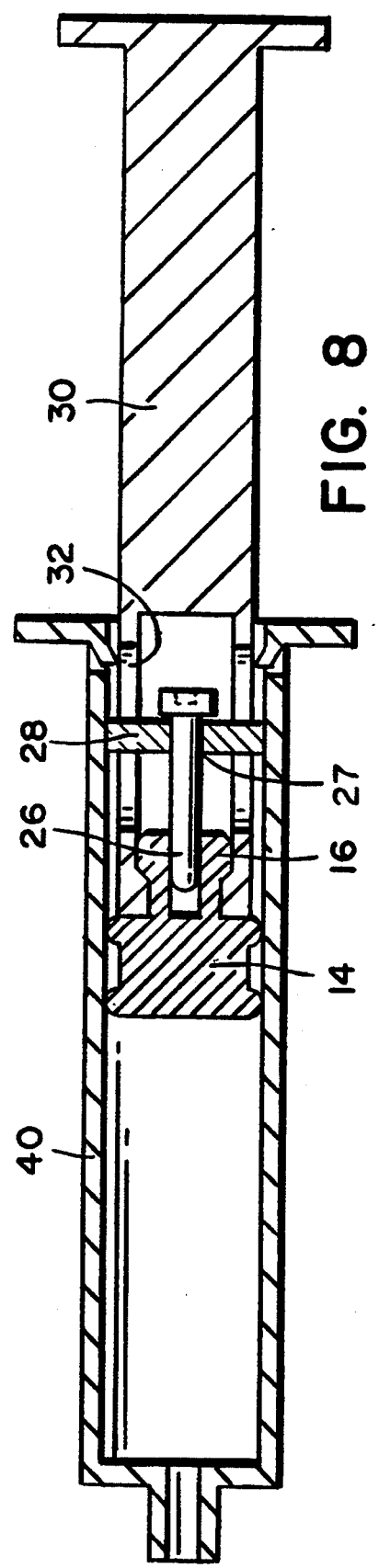

5,352,203

ASPIRATING NON-REUSEABLE SYRINGE

FIELD OF THE INVENTION

This invention relates in general to a plunger for a non-reuseable syringe, and more particularly to a non-reuseable syringe which is incapable of being used more than once for making an injection and yet is capable of aspirating fluids. The non-reuseable syringe utilizes a plunger that includes three connecting members which disconnect the plunger stem from the plunger piston after insertion of the plunger into the housing of the syringe in order to expel the contents of the syringe.

BACKGROUND OF THE INVENTION

In the United States and throughout the world, the multiple use of hypodermic syringe products which are intended for single use only is instrumental in drug abuse and more particularly in the transfer of contagious diseases. Such contagious diseases include AIDS and hepatitis. The transfer is most prevalent in intravenous drug users who routinely share and reuse syringes, but can also be a problem for the medical community if proper precautions to prevent multiple use of disposable syringes are not followed. Furthermore, the effects of multiple use are a major concern in third world countries where repeated use of syringe products may also be responsible for the spread of many diseases.

Many attempts have been made to remedy this problem. Some early attempted solutions involved destruction of the syringe after use either by using a destructive device or providing a syringe assembly with frangible zones so that the syringe could be rendered inoperable by the application of force. Although many of these devices work quite well, they require the specific intent of the user followed by the actual act to destroy or render the syringe inoperable. None of these devices is effective with a user having the specific intent to reuse the syringe.

Accordingly, there is a need for a non-reuseable syringe which becomes inoperative or incapable of further use automatically without an additional act on the part of the user. Co-owned U.S. Pat. No. 5,215,524, issued Jun. 1, 1993, the contents of which are hereby incorporated by reference, discloses a single use syringe which utilizes a disconnecting plunger stem. This syringe becomes inoperative automatically after a single use.

However, the need for a non-reuseable syringe must be met without preventing the filling or use of the syringe under normal conditions. One such use under normal conditions includes the ability to aspirate fluid using the syringe. It is common in the medical community to aspirate fluid during the use of a syringe (i.e., to alternately retract and extend the plunger of the syringe without expelling all contents of the syringe). This ability to aspirate must still be available with a single use syringe, and is not available with the syringe of U.S. Pat. No. 5,215,524.

Although various types of single use non-reuseable syringes have been proposed, the severity of the AIDS epidemic and the need for solutions to the above problems continuously provide a need for other types of non-reuseable syringes, particularly those which also provide for aspiration.

SUMMARY OF THE INVENTION

This continuous need is met, and the problems of multiple use of prior syringes overcome, by the plunger for a non-reuseable syringe of the subject invention, as well as by the syringe utilizing such plunger.

The main components of the plunger of the subject invention include a piston and a cylindrical plunger stem hollow at an open end thereof. The piston is removably connected to the cylindrical plunger stem by first, second, and third connecting members. The first connecting member is connected longitudinally to the piston and extends into the open end of the plunger stem. The first connecting member comprises a plurality of circumferentially spaced arms extending longitudinally away from the piston. The circumferentially spaced arms form a first aperture at an interior thereof and are flared at an exterior thereof on an end opposite the connection to the piston. The second connecting member comprises a plurality of protrusions extending radially away from a second aperture. The third connecting member is a longitudinal nipple slidable within the second aperture and matable with the first aperture formed by the circumferentially spaced arms of the first connecting member. The cylindrical plunger stem has a plurality of circumferentially spaced slots extending longitudinally at an open end thereof, and the open end of the hollow cylindrical plunger stem encloses the first, second and third connecting members such that the plurality of protrusions of the second connecting member slide within the plurality of slots and are friction fit within the inner diameter of an outer housing.

To accomplish the non-reuseable feature of the syringe which includes the plunger of the subject invention, an open end of the plunger stem is constricted on an interior thereof such that the interior snugly mates with the flared exterior of the circumferentially spaced arms when the nipple is inserted into the first aperture formed by the interior thereof.

When the piston which is located at the front end of the plunger is inserted into the rear end of a hollow cylindrical housing of a syringe unit, the wall and the piston form a sealed cavity (with the cylindrical housing side wall) for containing a liquid within the interior of the hollow cylindrical housing.

Prior to use, and preferably during manufacturing, the nipple is mated with the first aperture. When the nipple is mated with the first aperture, the second connecting member is positioned toward the front of the slots in the plunger stem. This allows the entire plunger unit to be drawn back for filling of the syringe, because in this configuration, the interior constricted portion of the cylindrical plunger stem exerts pressure on the circumferentially spaced arms. However, the nipple counteracts such pressure and prevents flexion of the arms inward. Therefore, the piston, plunger stem, and first, second and third connecting members operate as a single unit.

However, the nipple is forced from the first aperture as the protrusions on the second connecting member slide to the rear of the slots in the plunger stem. Any subsequent attempt to draw back the plunger to fill the syringe results in the interior constricted portion of the cylindrical plunger stem exerting pressure on the circumferentially spaced arms. Since the nipple no longer counteracts such pressure, the arms flex inward and the cylindrical plunger stem passes over the first connecting member. Thus, the plunger stem, second connecting member, and third connecting member are disconnected from the piston and the first connecting member. Accordingly, the syringe is incapable of being refilled because the piston must be withdrawn to create the vacuum for filling the syringe and to create the cavity for holding the liquid within the syringe.

The resulting non-reuseable single use syringe can thus be used to prevent multiple use of syringes, such as disposable hypodermic syringes. This is accomplished by providing the piston/syringe as discussed in further detail below.

The syringe according to the subject invention is also capable of aspiration due to the use of the sliding third connecting member (the nipple) within the second aperture. The nipple can slide within the aperture a distance equal to the length of the slots before the second connecting member (the plurality of protrusions) contacts the end of the slots and thereby forces the nipple out of the first aperture. Thus, one is able to move the plunger back and forth within the limitations of the slot length without disengaging the plunger stem. This allows for aspiration using the syringe as is also discussed in further detail below.

BRIEF DESCRIPTION OF THE FIGURES

These and other objects, features and advantages of this invention will be evident from the following detailed description of preferred embodiments when read in conjunction with the accompanying drawings in which:

FIG. 2 is a side view of a non-reuseable syringe including the plunger shown in FIG. 1, shown prior to withdrawal of the plunger to fill the syringe;

FIG. 3 is a cross sectional view of the non-reuseable syringe shown in FIG. 2;

FIG. 5 is a side view of the non-reuseable syringe of FIG. 2 indicating the position of the syringe elements during insertion of the plunger into the hollow cylindrical housing;

FIGS. 7 and 8 are side views of the non-reuseable syringe of FIG. 2 showing the aspiration feature of the syringe accomplished by sliding the nipple within the aperture without disconnecting the nipple from the aperture.

DETAILED DESCRIPTION OF THE INVENTION

Figure 1:
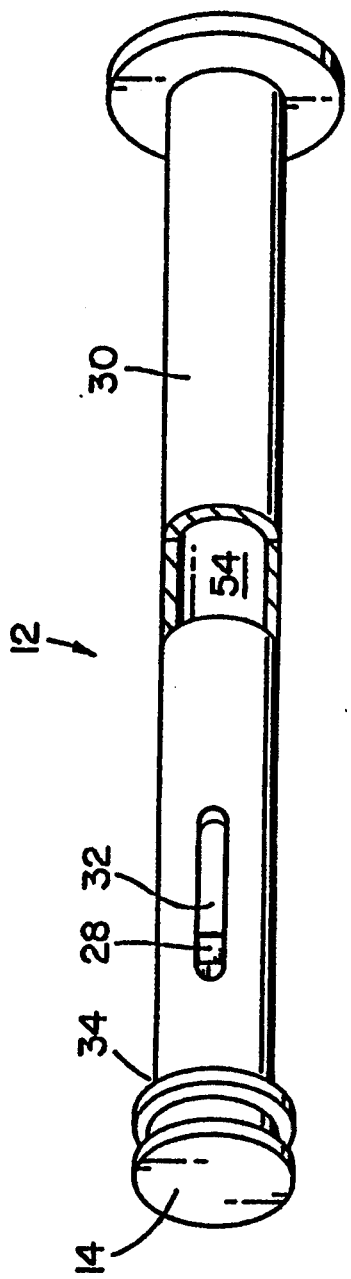
FIG. 1 is a partially cut away isometric view of a plunger which is one embodiment of the subject invention.
Figure 4:
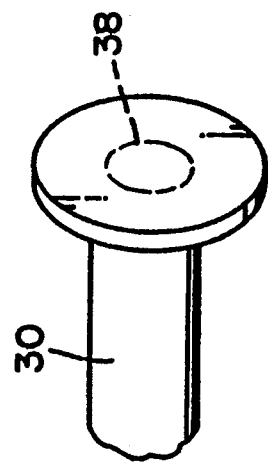
FIG. 4 is a partial isometric view of the rear end of the plunger shown in FIG. 1.

The main components of one preferred embodiment of the subject invention are depicted in FIGS. 1–8. As shown in FIGS. 1 and 4, the plunger 12 comprises a cylindrical plunger stem 30 closed at its rear end 38 and hollow at least at the other front end 34. At the front end 34 of the plunger stem 30 a piston 14 provides a liquid sealing means. The closed rear end 38 and the piston 14 form an interior 54 of the plunger 12. Toward the front end 34 of the plunger 12, slots 32 extend longitudinally around the circumference of the plunger stem.

Figure 6:
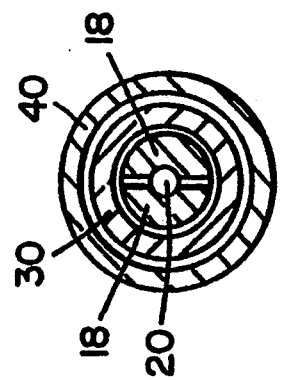
FIG. 6 is a cross sectional view of the non-reuseable syringe shown in FIG. 5.

The plunger stem 30 is connected to the piston 14 by a first connecting member 16, a second connecting member (made up of aperture 27 and protrusions 28), and a third connecting member 26. As shown in FIGS. 2 and 6, the first connecting member 16 is connected longitudinally to the piston 14, or may be integral therewith, and comprises a plurality of circumferentially spaced arms 18 extending longitudinally away from the piston 14. The arms 18 form a first aperture 20 at their interior, the purpose of which is discussed in further detail below. At the exterior end 22 of the arms away from the connection to the piston, the arms are flared. The first aperture 20 is mated with the third connecting member, a longitudinal nipple 26. The second connecting member includes a plurality of protrusions 28 which extend radially away from a second aperture 27 to form a friction fit within the inner diameter of an outer housing (see below) and also slideably fit within the slots 32 of the plunger stem 30. This is best shown in FIGS. 2 and 3. The nipple 26 slides within this second aperture 27. The interior surface at the front end of the plunger stem forms a constricted end 36, such that the front end 34 of the plunger stem 30 snugly fits against the arms 18 of the first connecting member 16. The flared end 22 of the first connecting member 16 mates with the constricted end 36 of the interior of the plunger stem 30 (see FIG. 2).

The plunger 12 is snugly inserted into a hollow cylindrical housing 40 of a syringe 10 (see FIGS. 2 and 5). The hollow cylindrical housing 40 is closed at its front end 42 by a wall 44, to which a needle can be mounted via a mounting means 48. Syringe needles are generally marketed with a plastic-type bracket on one end thereof. This plastic-type bracket mounts to the mounting means 48. The bracket may snugly slide over the mounting means 48, or the mounting means could be provided with grooves into which corresponding ridges on the bracket are twisted. Various means for connecting syringe needles are known in the art and can thus be used in the subject invention to mount a needle to the mounting means. A needle so mounted in the wall 44 is in fluid communication with the interior 46 (see FIG. 2) of the housing 40.

In order to prevent tampering with the connecting members in an attempt to reuse the syringe, removal of the plunger 12 is prevented by one-way flanges 52 at the rear end 50 of the housing 40. These flexible flanges are angled so that insertion of the plunger is possible but removal is not possible due to the contact of the protrusions 28 of the second connecting member 24 with the flanges 52. When the flanges extend into the interior of the housing, the diameter of the second connecting member protrusions 28, which are friction fit within the housing 40, is such that the second connecting member cannot pass through the housing at the position of the flanges.

Having described one embodiment of the plunger and non-reuseable syringe of the subject invention, its use is best illustrated in FIGS. 2 and 5, and 7 and 8. As shown in FIG. 2, the initial position of the elements of the syringe 10 prior to withdrawal (so as to fill the syringe) are illustrated. The plunger 12 is fully inserted into hollow cylindrical housing 40, so that the piston 14 is adjacent the wall 44 at the front end 42 of the housing 40. The nipple 26 is mated with the aperture 20 and the protrusions 28 are positioned slideably within and toward the front of the slots 32. A cross section illustrating the position of the syringe elements taken through the second connecting member is shown in FIG. 3. In this position, the nipple 26 prevents withdrawal of the plunger stem 30 without simultaneous withdrawal of the piston 14. This is because withdrawal of the plunger stem 30 causes the constricted front end 36 of the plunger stem 30 to exert a rearward force on the flared ends 22 of the first connecting member's arms 18. The nipple 26 prevents the arms 18 from flexing inward in response to this force. Accordingly, the entire plunger 12 unit is pulled rearward in one motion, so as to fill the syringe.

Upon forward motion of the plunger stem 30 to an extent greater than the length of the slot 32, as shown in FIG. 5, the second connecting member including the plurality of protrusions 28 slides to the rear of the slots 32 and the nipple 26 is no longer mated with the aperture 20. FIG. 6 illustrates a cross section of the syringe at the position of the flared ends of the arms at this point of an injection stroke. Any subsequent rearward movement of the plunger stem therefore results in another rearward force on the flared ends of the first connecting member's arms. The removal of the nipple allows the arms to flex inward, allowing the constricted end of the plunger stem to pass thereby. The plunger stem, second connecting member, and third connecting member are thus withdrawn, but the piston and first connecting member remain within the housing and no longer operate in conjunction with the plunger stem. As should be readily apparent, the syringe is then incapable of being used again because movement of the piston is necessary to create the vacuum for filling of the syringe.

FIGS. 7 and 8 illustrate the aspiration feature of the subject invention. The syringe (beginning as shown in FIG. 2) plunger stem 30 is withdrawn in the hollow cylindrical housing 40 to the point shown in FIG. 7. The plunger stem 30 is then pushed back into the hollow cylindrical housing 40 to the position shown in FIG. 8. At this point, the nipple 26 remains mated within the first aperture 20 of the first connecting member 16, by sliding within the second aperture 27 of the second connecting member. The plunger stem 30 can be alternately withdrawn and pushed into the hollow cylindrical housing 40 in this fashion for aspiration until the plurality of protrusions 28 of the second connecting member contact the rear of the slots 32. At that time, the second connecting member will pull the nipple 26 out of the first aperture 20 of the first connecting member 16 and render the syringe incapable of further use, as shown in FIG. 5.

Thus, the amount of aspiration possible can be controlled by controlling the length of the slots and the length of the longitudinal nipple. By extending the slot and providing a nipple which can slide within the second connecting member, this aspiration feature is attainable.

It should be readily apparent to those skilled in the art that any suitable materials, such as plastic and rubber, can be utilized for the various syringe elements.

The syringe which includes the plunger as described above is assembled as follows. The piston 14 and the first connecting member 16 are positioned at the front end 42 of the hollow cylindrical housing 40. The third connecting member 26 is positioned in the aperture 27 of the second connecting member, and both members so connected are then positioned within the cylindrical plunger stem 30 so that the protrusions 28 of the second connecting member extend through the slots 32 of the cylindrical plunger stem 30. At this point, the rear end 38 of the plunger stem 30 is not closed or sealed, but remains hollow (see broken lines on FIG. 4). The hollow cylindrical plunger stem 30, with the second and third connecting members positioned within the plunger stem, is snugly inserted into the hollow cylindrical housing 40 until the third connecting member 26 contacts the first connecting member 16 at the front of the hollow cylindrical housing 40. A rigid device, such as a wire or even a pencil-like member, is inserted into the hollow center 54 of the plunger stem 30 to exert a forward force on the third connecting member 26. This causes the nipple 26 (of the third connecting member) to mate with the first aperture 20 of the first connecting member 16. The rigid device is then removed from the center of the plunger stem, and the rear end 38 of the plunger stem is sealed or closed by suitable means. For example, a plastic plug may be inserted or injected, or a cap can be permanently applied to the end of the plunger stem. The end is permanently sealed so that future tampering with the second and third connecting members is not possible. This prevents the syringe from being "re-set", i.e., by forcing the third connecting member nipple forward to mate with the first aperture. After the end of the plunger stem is sealed, the syringe is ready for use. Accordingly, after any required aspiration and a single dispensing use, the syringe of the subject invention cannot be used again because the plunger stem separates from the piston. This prevents subsequent filling with liquid.

The subject invention thus provides a method of preventing multiple use of a syringe comprising the steps of: selecting the single use syringe of the subject invention as disclosed above; drawing a liquid into the single use syringe; and dispensing the liquid from the single use syringe. When the liquid has been dispensed from the single use syringe, the syringe cannot again be used to draw a liquid into the syringe due to the separation of the piston from the plunger stem upon any subsequent withdrawal of the plunger body. The invention also provides a method of aspirating using a single use syringe by alternately pushing and drawing the plunger without unmating the nipple of the syringe.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A plunger for an aspirating single use syringe comprising:
   a cylindrical plunger stem being hollow at an open end thereof, said plunger stem having a plurality of circumferentially spaced slots extending longitudinally at said open end thereof and being constricted on an interior of said open end thereof;
   a piston attached to said open end of said plunger stem;
   a first connecting member connected to said piston and extending into said open end of said plunger stem, said first connecting member comprising a plurality of circumferentially spaced arms extending longitudinally away from said piston, said circumferentially spaced arms forming a first aperture at an interior thereof and said circumferentially spaced arms flared at an exterior thereof on an end opposite said connection to said piston;
   a second connecting member comprising a plurality of protrusions extending radially away from a second aperture, said second connecting member positioned within said plunger stem so that said plurality of protrusions slide within said plurality of slots; and a third connecting member comprising a longitudinal nipple slidable within said second aperture and matable with said first aperture, wherein when said nipple is mated with said first aperture, the flared circumferentially spaced arms of said first connecting member snugly mate with said constricted interior of said plunger stem.

2. The plunger of claim 1 wherein said first connecting member is integral with said piston.

3. An aspirating single use syringe comprising:

a hollow cylindrical housing closed at its front end by a wall so as to form an interior thereof;

means for mounting a needle in said wall, wherein when said needle is mounted in said wall, said needle is in fluid communication with the interior of said hollow cylindrical housing; and a plunger, said plunger comprising:
  a cylindrical plunger stem being hollow at an open end thereof, said plunger stem having a plurality of circumferentially spaced slots extending longitudinally at said open end thereof and being constricted on an interior of said open end thereof;
  a piston attached to said open end of said plunger stem;
  a first connecting member connected to said piston and extending into said open end of said plunger stem, said first connecting member comprising a plurality of circumferentially spaced arms extending longitudinally away from said piston, said circumferentially spaced arms forming a first aperture at an interior thereof and said circumferentially spaced arms flared at an exterior thereof on an end opposite said connection to said piston;
  a second connecting member comprising a plurality of protrusions extending radially away from a second aperture, said second connecting member positioned within said plunger stem so that said plurality of protrusions slide within said plurality of slots; and
  a third connecting member comprising a longitudinal nipple slidable within said second aperture and matable with said first aperture, wherein when said nipple is mated with said first aperture, the flared circumferentially spaced arms of said first connecting member snugly mate with said constricted interior of said plunger stem, said piston of said plunger snugly inserted into an open rear end of said hollow cylindrical housing and slidable within said hollow cylindrical housing, and said radial extension of said plurality of protrusions contacting the interior of said hollow cylindrical housing such that said second connecting member friction fits within said interior of said hollow cylindrical housing.

4. A method of preventing multiple use of a syringe which method comprises the steps of:

selecting the single use syringe of claim 3 for dispensing a liquid therefrom;

positioning said nipple within said first aperture and drawing a liquid into said single use syringe, wherein said drawing comprises drawing said plunger away from said front end of said hollow cylindrical housing, causing said protrusions to position at a forward end of said slots; and dispensing the liquid from the single use syringe, wherein said dispensing comprises pushing said plunger toward said front end of said hollow cylindrical housing, causing said protrusions to position at a rearward end of said slots thereby removing said nipple from said first aperture; wherein when said liquid has been dispensed from said single use syringe, said syringe cannot again be used to draw a liquid into said syringe due to the removal of said nipple from said first aperture, such that subsequent drawing of said plunger causes said constricted interior on the front end of said plunger stem to compress said flared exterior of said circumferentially spaced arms, thereby disengaging said plunger stem from said piston and said first connecting member.

5. A method of preventing multiple use of an aspirating syringe which method comprises the steps of:

selecting the single use syringe of claim 3 for aspirating and dispensing a liquid therefrom;

positioning said nipple within said first aperture and drawing a liquid into said single use syringe, wherein said drawing comprises drawing said plunger away from said front end of said hollow cylindrical housing, causing said protrusions to position at a forward end of said slots;

alternately pushing said plunger toward said front end of said hollow cylindrical housing and drawing said plunger away from said front end of said hollow cylindrical housing, such that said nipple slides within said second aperture and said protrusions slide within said slots without contacting said rearward end of said slots, thereby aspirating with said single use syringe; and dispensing the liquid from said single use syringe by pushing said plunger toward said front end of said hollow cylindrical housing and contacting said protrusions with said rearward end of said slots, thereby removing said nipple from said first aperture; wherein when said liquid has been dispensed from said single use syringe, said syringe cannot again be used to draw a liquid into said syringe due to the removal of said nipple from said first aperture, such that subsequent drawing of said plunger causes said constricted interior on the front end of said plunger stem to compress said flared exterior of said circumferentially spaced arms, thereby disengaging said plunger stem from said piston and said first connecting member.

* * * * *